US008500641B2

United States Patent
Raju et al.

(10) Patent No.: US 8,500,641 B2
(45) Date of Patent: Aug. 6, 2013

(54) APPARATUS AND METHOD FOR 3D ULTRASOUND IMAGING AND THERAPY

(75) Inventors: Balasundara Raju, Tarrytown, NY (US); Christopher Hall, Hopewell Junction, NY (US); Chien Ting Chin, Tarrytown, NY (US); William T. Shi, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 306 days.

(21) Appl. No.: 12/516,598

(22) PCT Filed: Nov. 6, 2007

(86) PCT No.: PCT/IB2007/054507
§ 371 (c)(1),
(2), (4) Date: May 28, 2009

(87) PCT Pub. No.: WO2008/065561
PCT Pub. Date: Jun. 5, 2008

(65) Prior Publication Data
US 2010/0069754 A1    Mar. 18, 2010

Related U.S. Application Data

(60) Provisional application No. 60/867,464, filed on Nov. 28, 2006, provisional application No. 60/887,640, filed on Feb. 1, 2007.

(51) Int. Cl.
*A61B 8/00* (2006.01)
*A61N 7/00* (2006.01)

(52) U.S. Cl.
USPC .................... 600/439; 600/459; 601/2; 601/3

(58) Field of Classification Search
USPC .............. 600/439, 443, 459; 601/2–4; 604/22
See application file for complete search history.

(56) References Cited

U.S. PATENT DOCUMENTS

| 4,757,820 A | 7/1988 | Itoh |
| 5,316,000 A | 5/1994 | Chapelon |
| 5,391,140 A | 2/1995 | Schaetzle |
| 5,471,988 A | 12/1995 | Fujio |
| 5,558,092 A | 9/1996 | Unger |
| 5,769,790 A | 6/1998 | Watkins |

(Continued)

FOREIGN PATENT DOCUMENTS

| WO | 9922652 A1 | 5/1999 |
| WO | 2006042201 A1 | 4/2006 |
| WO | 2006097661 A1 | 9/2006 |

*Primary Examiner* — Ruth S Smith

(57) ABSTRACT

An apparatus for application of three-dimensional ultrasound imaging and therapy comprising a two-dimensional ultrasound imaging array of transducer elements having an image signal transmitter and receiver that forms, steers and selectively focuses ultrasound beams to a three-dimensional moving or stationary spatial volume; one or more two-dimensional ultrasound therapy arrays of transducer elements, each array having a therapy signal transmitter that forms, steers and selectively focuses and delivers ultrasound therapy to the volume; wherein the location of the array of imaging and therapy transducer elements are known relative to one another; and a controller that controls the image transmitter and receiver to provide three-dimensional images of the volume and simultaneously independently controls each of the one or more therapy transmitters to deliver therapy to the volume. Also disclosed is a method of delivering ultrasound therapy to a biological tissue in a three-dimensional moving or stationary spatial volume utilizing the apparatus.

7 Claims, 1 Drawing Sheet

U.S. PATENT DOCUMENTS

| | | |
|---|---|---|
| 6,309,355 B1 | 10/2001 | Cain |
| 6,425,867 B1 | 7/2002 | Vaezy |
| 6,428,477 B1 | 8/2002 | Mason |
| 6,488,630 B1 * | 12/2002 | Hand et al. .................... 600/459 |
| 6,500,121 B1 | 12/2002 | Slayton |
| 6,537,224 B2 | 3/2003 | Mauchamp |
| 6,716,188 B2 | 4/2004 | Noda |
| 6,719,694 B2 | 4/2004 | Weng |
| 6,726,627 B1 | 4/2004 | Lizzi |
| 2004/0068186 A1 | 4/2004 | Ishida |
| 2006/0058707 A1 | 3/2006 | Barthe |
| 2006/0241442 A1 * | 10/2006 | Barthe et al. .................. 600/439 |
| 2007/0073135 A1 | 3/2007 | Lee |

* cited by examiner

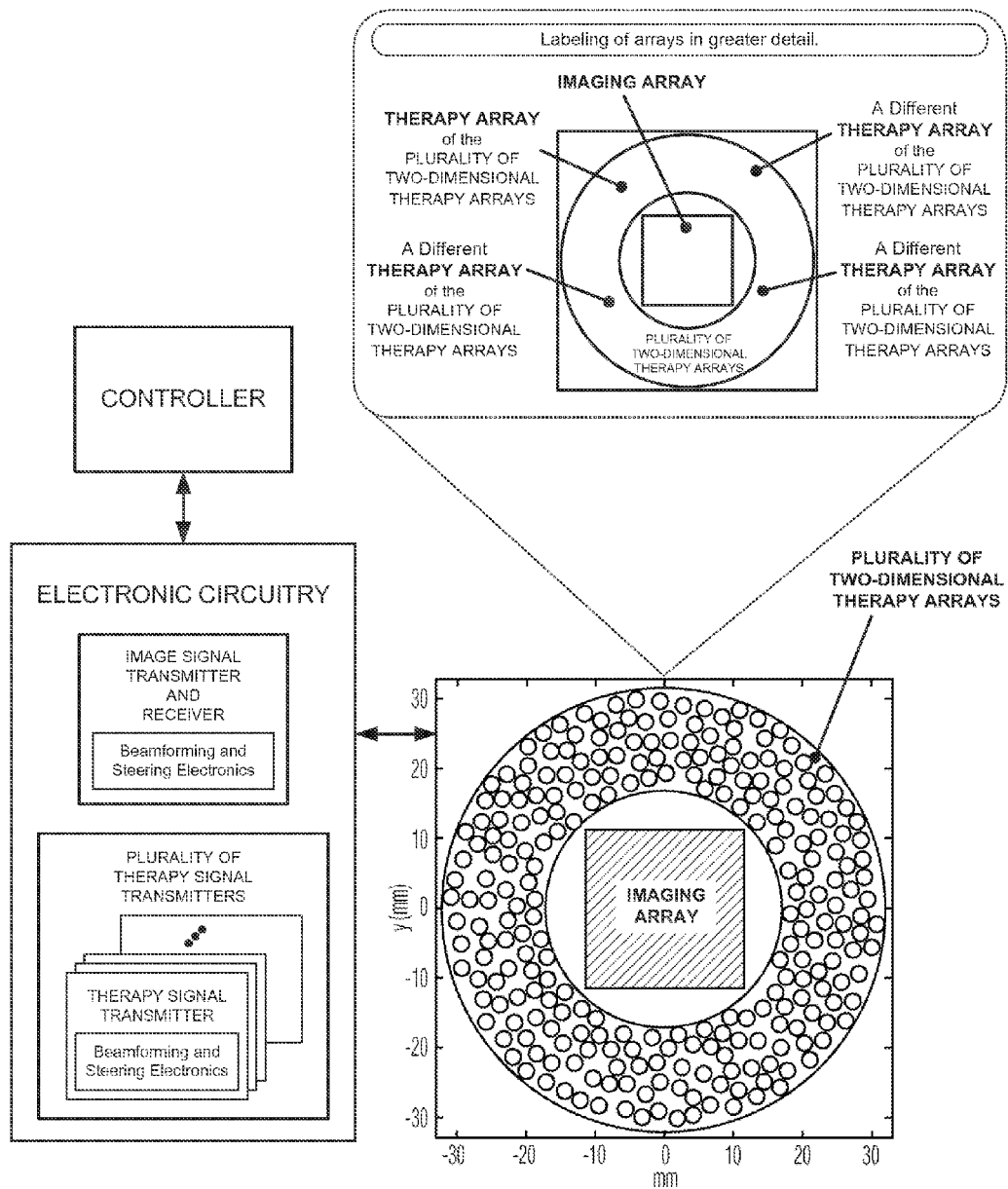

APPARATUS AND METHOD FOR 3D ULTRASOUND IMAGING AND THERAPY

CROSS REFERENCE TO RELATED CASES

Applicants claim the benefit of Provisional Application Ser. No. 60/867,464, filed Nov. 28, 2006.

The invention relates to an apparatus containing two separate two-dimensional (2D) ultrasound array transducers, one for providing three-dimensional (3D) images, and the other for generating therapy beams that can be electronically steered in three dimensions; and the use of the apparatus in delivering ultrasound mediated therapy such as localized gene delivery, drug delivery, sonothrombolysis, tissue ablation etc.

Ultrasound has many therapeutic applications such as tissue ablation, drug delivery, hyperthermia, clot dissolution, etc. Single element therapy transducers are limited by a fixed focal length, and depend on mechanical translation to treat different regions of the body. In order to steer the therapy beam to different locations in the body, electronically phased array transducers may be employed. Simultaneous imaging of tissues during therapy makes it possible to plan and monitor the treatment.

One example of a combined therapy and imaging system is described by US patent Nock et al (U.S. Pat. No. 6,716,188). This patent describes a system for drug delivery enhancement and imaging comprising a transducer having only one linear array of elements.

U.S. Pat. No. 5,558,092 (Unger et al) discloses one example of a combined ultrasound imaging and therapy system with separate transducers on the same substrate. Several transducer configurations are proposed including one that has a 2D matrix of elements for both the imaging and therapy that are operated in a multiplexed manner such that a sequential linear set of elements are activated.

U.S. Pat. No. 6,428,477 (Mason) assigned to Philips, describes a fully steerable two-dimensional ultrasound array that delivers therapy by steering and selective focusing of beams. Same transducer is used for both therapy and imaging.

U.S. Pat. No. 6,719,694 describes ultrasound transducers that perform both therapy and imaging. A quality factor circuit changes the bandwidth of the transducer such that high bandwidth operation is used in imaging.

U.S. Pat. No. 6,500,121 describes an ultrasonic therapy system having a single transducer that performs imaging, therapy, and temperature monitoring, where the single transducer can be operated to provide imaging or therapy in a 3D manner.

The method of Unger et al uses multiplexed linear elements (U.S. Pat. No. 5,558,092). The therapy array is not configured to perform 3D steering of the beam and only provides shallow operation near the skin surface. Moreover, the same substrate is used for both the imaging and therapy arrays. This leads to the possibility of cross talk between the two arrays especially since the therapy array commonly utilizes higher power levels. Also, imaging array is fixed and cannot be swapped with other imaging probes for the same therapy array. Using the same substrate for both the arrays leads to less optimal use of the piezo material, since therapy arrays might benefit from being made of piezocomposite materials where arbitrary elements size and shapes can be made.

The method of Mason (U.S. Pat. No. 6,428,477), Weng (U.S. Pat. No. 6,719,694) and Slayton et al (U.S. Pat. No. 6,500,121) uses the same transducer for imaging and therapy. However, therapy and imaging have different requirements since the focusing capabilities and frequency requirements are different. It is often difficult to optimize the transducer for both the applications. For example, ultrasound imaging typically employs frequencies greater than 2 MHz, whereas therapy employs frequencies less than two MHz. For small animal studies, even higher frequencies such as 15 MHz are preferred for imaging. The small aperture sizes of imaging transducers are insufficient to achieve focusing gains needed for therapy that usually requires much larger transducers. Moreover the imaging array has regularly spaced elements and if used for therapy would require a large number of elements in order to accommodate the requirement to avoid grating lobes.

However, as discussed above, problems still persist with these systems and methodology in ultrasound imaging and therapy, particularly for biological tissue in a spatial volume which may be in motion, which are overcome by the apparatus and methodology disclosed herein.

According to this invention, herein disclosed is an apparatus containing two separate two-dimensional (2D) ultrasound array transducers, one for providing three-dimensional (3D) images, and the other for generating therapy beams that can be electronically steered in three dimensions; and the use of the apparatus in delivering ultrasound mediated therapy such as localized gene delivery, drug delivery, sonothrombolysis, tissue ablation.

Specifically, it is an object of the invention to provide an apparatus for application of three-dimensional ultrasound imaging and therapy comprising:

a two-dimensional ultrasound imaging array of transducer elements having an image signal transmitter and receiver that forms, steers and selectively focuses ultrasound beams to a three-dimensional moving or stationary spatial volume;

one or more two-dimensional ultrasound therapy arrays of transducer elements, each array having a therapy signal transmitter that forms, steers and selectively focuses and delivers ultrasound therapy to the volume; wherein the location of the array of imaging and therapy transducer elements are known relative to one another; and a controller that controls the image transmitter and receiver to provide three-dimensional images of the volume and simultaneously independently controls each of the one or more therapy transmitters to deliver therapy to the volume.

Another object of the invention is to provide an apparatus further comprising each of the imaging and therapy transducer arrays having a plurality of ultrasound elements that are individually controllable in amplitude, phase and frequency of operation.

Another object of the invention is to provide an apparatus further comprising the controller correlating the imaged volume with the therapy transducer array so that the therapy is delivered to the volume.

Another object of the invention is to provide an apparatus further comprising the therapy transducer array located in a two-dimensional annular space between two concentric circles and the imaging transducer array located within the two-dimensional space of the inner circle.

Another object of the invention is to provide an apparatus further comprising the therapy transducer array fixedly attached to a side of the imaging transducer array.

Another object of the invention is to provide an apparatus further comprising a plurality of therapy transducer arrays located in a two-dimensional annular space between two concentric circles and the imaging transducer array located within the two-dimensional space of the inner circle, wherein each of the plurality of therapy arrays is capable of providing therapy in different spatial volumes, different therapy regimens including different ultrasound wave frequencies and different tissue penetration depths.

Another object of the invention is to provide a method of delivering ultrasound therapy to a biological tissue in a three-dimensional moving or stationary spatial volume comprising:

imaging the volume utilizing an apparatus for application of three-dimensional ultrasound imaging and therapy, the apparatus comprising:

a two-dimensional ultrasound imaging array of transducer elements having an image signal transmitter and receiver that forms, steers and selectively focuses ultrasound beams to a three-dimensional moving or stationary spatial volume;

one or more two-dimensional ultrasound therapy arrays of transducer elements, each array having a therapy signal transmitter that forms, steers and selectively focuses and delivers ultrasound therapy to the volume; wherein the location of the array of imaging and therapy transducer elements are known relative to one another; and a controller that controls the image transmitter and receiver to provide three-dimensional images of the volume and simultaneously independently controls each of the one or more therapy transmitters to deliver therapy to the volume;

delivering the therapy to the tissue utilizing the apparatus.

Another object of the invention is to provide a method further comprising each of the imaging and therapy transducer arrays having a plurality of ultrasound elements that are individually controllable in amplitude, phase and frequency of operation.

Another object of the invention is to provide a method further comprising the controller co-registering the imaged volume with the therapy transducer array so that the therapy is delivered to the volume.

Another object of the invention is to provide a method further comprising the therapy transducer array located in a two-dimensional annular space between two concentric circles and the imaging transducer array located within the two-dimensional space of the inner circle.

Another object of the invention is to provide a method further comprising the therapy transducer array fixedly attached to a side of the imaging transducer array.

Another object of the invention is to provide a method further comprising a plurality of 2D therapy transducer arrays located in a two-dimensional annular space between two concentric circles and the imaging transducer array located within the two-dimensional space of the inner circle, wherein each of the plurality of 2D therapy arrays is capable of providing therapy (i.e., via a controller controlling, with use of electronic circuitry, one or more corresponding therapy transmitters for respective 2D therapy arrays to deliver therapy) in different spatial volumes, different therapy regimens including different ultrasound wave frequencies and different tissue penetration depths.

Another object of the invention is to provide a method further comprising delivering ultrasound therapy to a biological tissue selected from the group consisting of brain lesions, uterine fibroids, liver tumor, breast tumor, other tumors of the mammalian body and blood clots.

These and other aspects of the invention are explained in more detail with reference to the following embodiments and with reference to the figures.

FIG. 1 depicts an embodiment of the apparatus having a combined 2D therapy and 2D imaging array or probe. The imaging array in the shape of a square is placed at the center of the annular hole and the therapy array having numerous elements shown as circles are in the annulus surrounding the imaging array.

In any non-invasive therapy application, planning, guidance, and monitoring are critical. This invention provides three important benefits to these goals: fast real-time three dimensional interrogation of the 3D spatial volume surrounding the target biological tissue, accurate and precise correlation or co-registration of the ultrasound therapy or treatment beam(s) to the ultrasound 3D imaging information and near-real-time adjustment of both the size and shape of the 3D spatial volume target zone containing the biological tissue of interest and the path of the treatment beam(s). For example, in the treatment of the heart, the movement of the target tissue may be complicated and irregular due to respiration motion and arrhythmia. The imaging array can image (i.e., via the controller controlling, with the use of electronic circuitry, beamforming and steering electronics of the image signal transmitters and receivers of the imaging array to image a volume) in real time this motion, then the therapy array can be programmed to deliver (i.e., via the controller controlling, with use of electronic circuitry, beamforming and steering electronics of one or more corresponding therapy transmitters for respective 2D therapy arrays) the therapeutic ultrasound with temporal gating and/or spatial steering so that the treatment zone coincides with the target volume.

According to the invention herein, the apparatus contains two separate 2D ultrasound array transducers, one for providing 3D images, and the other for providing therapy beam that is electronically steerable in three dimensions; the individual elements of both arrays are distributed along two dimensions, and are individually controllable in amplitude, phase, and frequency of operation. The elements of both the imaging and therapy arrays could be distributed in a random or irregular manner over the surface. The two arrays can use separate beam formers for steering and focusing. The two arrays allow the 3D images and therapy beams to be registered or correlated with respect to each other.

In one embodiment, the therapy array consists of a 2D spherical annulus. The hole in the annulus provides space for the imaging array. The elements of the therapy array are circular in shape and randomly distributed throughout the array. FIG. 1 shows the therapeutic array with the imaging array at the center. This embodiment provides a simple implementation for the registration of the therapy probe in the space of the image provided by the imaging array. The imaging probe could be any matrix transducer such as the X3-1 transducers sold by Philips.

In another embodiment, the 2D imaging array is attached to the side of the therapy array and fixed with respect to it. The two arrays are rigidly fixed with respect to each other and hence the registration information is known a priori.

In another embodiment, an arrangement of several therapy arrays is used with one imaging transducer. The different 2D therapy arrays could be located around the imaging array in a circular fashion. Each 2D therapy array may provide treatment (i.e., via the controller controlling beamforming and steering electronics of a therapy transmitter for a respective 2D therapy array) in different spatial regions or different treatment regiments such as frequencies and penetration depth. The imaging array would provide a wide field of view for planning purpose. One or more of the 2D therapy arrays would be turned on (i.e., via the controller controlling beamforming and steering electronics of a therapy transmitter for a respective 2D therapy array) to activate the therapy based on spatial location and depth of the treatment region, available acoustic window and other factors.

The controller that controls and co-registers the ultrasound therapy delivery with 3D images provided by the ultrasound image transmitter and receiver can include one or more computers or processors. The beam forming and steering electronics (i.e., "Beamforming and Steering Electronics" of (i) the image signal transmitter and receiver and (ii) each therapy signal transmitter of the plurality of therapy signal transmitters as shown in FIG. 1) controlled by the controller are conventional and can be operated according to computer programs known to one skilled in the art. The therapy system consists of an array of piezo-electric, piezo-composite, crystal, or ceramic elements capable of generating either a high, low duty cycle or a lower, longer duty cycle pressure field. The transducer elements are excited by a voltage supplied by a high power amplifier and generated by either an arbitrary wave or a single frequency source. The timing of these signals is controlled by either programmable trigger circuitry or a therapeutic beam former. The commencement and cessation of therapy pressure field can be controlled through programmable triggers, controlled externally, or from a derived trigger event from the 2D imaging array (e.g. when the desired tissue volume is within a specific spatial location). The entire system consisting of both therapeutic and imaging arrays and corresponding electronic circuitry (amplifiers, power supplies, signals sources, beam formers, trigger circuitry (i.e., "Electronic Circuitry" as shown in FIG. 1)) is controlled by a external controller, usually a personal computer. This external controller is the master controller of most timing events, user interaction, and integration of the imaging and therapy probe.

Ultrasound therapy is an emerging application and business opportunity. Currently ultrasound therapy is used routinely in cancer treatment in China; in the USA it is approved by the FDA for the treatment of uterine fibroid and in trials for prostate cancer and benign prostate hyperplasia; and in Europe clinical trials are on-going.

The invention can be used in many application areas for delivering ultrasound therapy, for example in treating hyperthermia, high intensity focused ultrasound (HIFU), and microbubble/nanoparticle-mediated therapy. The last application area exploits acoustically induced bioeffects to enhance and control localized gene and drug delivery, such as delivery of high intensity ultrasound beams to cause previously injected microspheres containing a drug substance to burst at the tissue site releasing the drug substance; and other applications in the field of ultrasound mediated molecular medicine. This area also includes the use of ultrasound to enhance the efficacy of thrombolytic agents used in an acute setting following an atherosclerotic event. The application can also be used where ultrasound is used for clot dissolution for stroke or DVT patients.

The invention can be used in any areas where focused ultrasound may provide therapeutic effects. Typical examples include brain lesions, uterine fibroids, liver tumor, breast tumor and other tumors of the mammalian body and blood clots. In the cardiac setting, novel applications are being developed to protect the heart prior to or subsequent to a myocardial infarction.

While the present invention has been described with respect to specific embodiments thereof, it will be recognized by those of ordinary skill in the art that many modifications, enhancements, and/or changes can be achieved without departing from the spirit and scope of the invention. Therefore, it is manifestly intended that the invention be limited only by the scope of the claims and equivalents thereof.

The invention claimed is:

1. An apparatus for application of three-dimensional ultrasound imaging and therapy comprising:
    a controller;
    a two-dimensional ultrasound imaging array of transducer elements coupled to beamforming and steering electronics of an image signal transmitter and receiver that forms, steers and selectively focuses ultrasound beams to provide three-dimensional images of a three-dimensional moving or stationary spatial volume in response to being controlled by the controller; and
    a plurality of two-dimensional ultrasound therapy arrays of transducer elements, each array coupled to beamforming and steering electronics of a therapy signal transmitter that forms, steers and selectively focuses and delivers ultrasound therapy to the volume in response to being controlled by the controller; wherein the location of the array of imaging and therapy transducer elements are known relative to one another, further wherein the plurality of two-dimensional ultrasound therapy arrays of transducer elements is located in a two-dimensional annular space between two concentric circles, wherein the elements of the plurality of two-dimensional ultrasound therapy arrays are (a) circular in shape and (b) randomly distributed throughout the respective therapy array, and the two-dimensional imaging array of transducer elements is located within a two-dimensional space of an inner circle of the two concentric circles, further wherein the plurality of two-dimensional ultrasound therapy arrays comprises different two-dimensional therapy arrays located around the imaging array in a circular fashion, the different two-dimensional therapy arrays for providing (i) therapy in different spatial volumes, (ii) different therapy regimens including different ultrasound wave frequencies and (iii) different tissue penetration depths,
    wherein the controller controls the beamforming and steering electronics of the image transmitter and receiver to provide three-dimensional images of the volume and simultaneously independently controls beamforming and steering electronics of each of the plurality of therapy transmitters to deliver therapy to the volume.

2. The apparatus of claim 1, wherein each of the imaging and therapy transducer arrays have a plurality of ultrasound elements that are individually controllable in amplitude, phase and frequency of operation.

3. The apparatus of claim 1, wherein the controller co-registers the imaged volume with the plurality of two-dimensional therapy transducer arrays so that the therapy is delivered to the volume.

4. A method of delivering ultrasound therapy to a biological tissue in a three-dimensional moving or stationary spatial volume comprising:
    imaging the volume utilizing an imaging functionality of an apparatus for application of three-dimensional ultrasound imaging and therapy, wherein the apparatus comprises (i) a controller, (ii) a two-dimensional ultrasound imaging array of transducer elements coupled to beamforming and steering electronics of an image signal transmitter and receiver that forms, steers and selectively focuses ultrasound beams to provide three-dimensional images of a three-dimensional moving or stationary spatial volume in response to being controlled by the controller; and (iii) a plurality of two-dimensional ultrasound therapy arrays of transducer elements, each array coupled to beamforming and steering electronics of a therapy signal transmitter that forms, steers and selectively focuses and delivers ultrasound therapy to the volume in response to being controlled by the controller; wherein the location of the array of imaging and therapy transducer elements are known relative to one another, further wherein the plurality of two-dimensional ultrasound therapy arrays of transducer elements is located in a two-dimensional annular space between two concentric circles, wherein the elements of the plurality of two-dimensional ultrasound therapy arrays are (a) circular in shape and (b) randomly distributed throughout the respective therapy array, and the two-dimensional imaging array of transducer elements is located within a two-dimensional space of an inner circle of the two concentric circles, further wherein the plurality of two-dimensional ultrasound therapy arrays comprises different two-dimensional therapy arrays located around the imaging array in a circular fashion, the different two-dimensional therapy arrays for providing (a) therapy in different spatial volumes, (b) different therapy regimens including different ultrasound wave frequencies and (c) different tissue penetration depths, wherein the controller controls the beamforming and steering electronics of the image transmitter and receiver to provide three-dimensional images of the volume and simultaneously independently controls beamforming and steering electronics of each of the plurality of therapy transmitters to deliver therapy to the volume; and delivering the ultrasound therapy to the tissue of the imaged volume utilizing a therapy functionality of the apparatus.

5. The method of claim 4, further comprising controlling a plurality of ultrasound elements that are individually controllable in amplitude, phase and frequency of operation for each of the imaging and therapy transducer arrays during imaging of the volume and delivering of the ultrasound therapy, respectively.

6. The method of claim 4, further comprising co-registering, via the controller, the imaged volume with the plurality of two-dimensional therapy transducer arrays so that the therapy is delivered to the specified volume.

7. The method of claim 4, wherein delivering the ultrasound therapy comprises delivering the ultrasound therapy to a biological tissue selected from the group consisting of brain lesions, uterine fibroids, liver tumor, breast tumor, tumors of a mammalian body and blood clots.

* * * * *